US009433535B2

(12) United States Patent
Crago (10) Patent No.: US 9,433,535 B2
(45) Date of Patent: Sep. 6, 2016

(54) MODALITY AND SYSTEM FOR CASTING DIABETIC AND NEUROPATHIC PLANTAR FOOT ULCERATIONS AND TREATING DEFECTS THAT LIMIT RANGE OF MOTION

(76) Inventor: Michael G Crago, Littleton, CO (US)

( * ) Notice: Subject to any disclaimer, the term of this patent is extended or adjusted under 35 U.S.C. 154(b) by 251 days.

(21) Appl. No.: 13/066,439

(22) Filed: Apr. 14, 2011

(65) Prior Publication Data

US 2012/0265113 A1     Oct. 18, 2012

(51) Int. Cl.
*A61F 5/00* (2006.01)
*A61F 13/04* (2006.01)
*A61F 15/00* (2006.01)
*A61F 13/00* (2006.01)

(52) U.S. Cl.
CPC ........... *A61F 13/043* (2013.01); *A61F 15/006* (2013.01); *A61F 2013/00621* (2013.01)

(58) Field of Classification Search
CPC ................ B60B 2310/316; B60B 2900/521; B60B 2900/531; B60B 33/0028; B60B 33/0042; Y10T 16/216; Y10T 29/49826; A01D 46/08; A01D 46/14; A01K 13/006; A01K 13/007; A41B 11/001; A41B 11/002; A61F 5/0111; A61F 5/0195; A61F 5/0127; A61F 13/043; A61F 2005/0167; A61F 2005/0179; A61F 13/04; A61F 13/045; A61F 15/006; A61F 2013/00621; A61F 2210/0085; A61F 2/604; A61F 5/05; A61F 5/0585; A43B 7/28; B29C 35/0222; B29C 43/00
USPC .............. 602/23–28, 43, 62–63, 65–66, 900, 602/903, 5–8; 128/882, 892, 898; 5/648–651
See application file for complete search history.

(56) References Cited

U.S. PATENT DOCUMENTS 2,582,242 A *   1/1952   Eberl ................................ 602/8
6,974,431 B2 * 12/2005   Jensen et al. ..................... 602/8

* cited by examiner

*Primary Examiner* — Michael Brown (57) ABSTRACT

A system that is clinically and effically sound, consisting of proprietary components that not only address the needs of the clinician but are universally utilized in a concise protocol covering a wide range of indications and conditions.

8 Claims, 10 Drawing Sheets

MODALITY AND SYSTEM FOR CASTING DIABETIC AND NEUROPATHIC PLANTAR FOOT ULCERATIONS AND TREATING DEFECTS THAT LIMIT RANGE OF MOTION

RELATED APPLICATIONS

The present application is related to U.S. Pat. No. 6,974,431, issued Dec. 12, 2005, included by reference herein.

The present application is related to U.S. Pat. No. 4,817,590, issued Apr. 4, 1989, included by reference herein.

The present application is related to U.S. Pat. No. 4,235,228, issued Nov. 25, 1980, included by reference herein.

The present application is related to U.S. Pat. No. 3,900,024, issued Aug. 19, 1975, included by reference herein.

The present application is related to U.S. Pat. No. 3,415,243, issued Dec. 10, 1968, included by reference herein.

The present application is related to U.S. Pat. No. 3,307,537, issued Mar. 7, 1967, included by reference herein.

No known patents for serial casting

FIELD OF THE INVENTION

The present invention relates to total contact casting and, more particularly, to a unique turn key, user friendly modality that provides intimate contact, and promotes better body mechanics, which have proven to be the key components in healing diabetic and neuropathic foot ulceration. The system accommodates a variety of conditions that lead to range of motion disorders and allows the condition to be treated while maintaining quality of life.

BACKGROUND OF THE INVENTION

Diabetic and neuropathic foot ulcerations can be challenging wounds to heal. The etiology of these ulcerations can vary from compromised blood flow to arthritis, and other conditions and co-morbidities. Total contact casts have been utilized for decades for the treatment of diabetic, neuropathic foot ulcerations, as well as charcot foot deformities.

Total Contact Casting was introduced to the United States nearly 70 years ago from the leper colonies of India and was adopted by our clinicians for the treatment of neuropathic and diabetic foot ulcerations. The total contact cast configuration and application protocol has remained almost exactly the same since the introduction with the exception of new lighter weight materials. This approach to total contact casting is the first new cast configuration that is truly unique from all other systems and has proven to be clinically effective.

Total Contact Casting as described in the name is meant to have as close to intimate contact with the patients leg as possible. This intimate contact is designed to secure the foot and leg in a position that allows for the patient to ambulate while removing the pressure and propulsive forces from the wound and not allowing the foot to move in the cast. The total contact cast should be applied weekly with the exception of the first week at which the cast should be re-applied during the first 48 to 72 hours to accommodate the reduction of swelling and edema in the leg.

A typical total contact cast is applied in several layers. These layers are comprised of a stockinette, a felt pad covering the length of the tibia, a pad covering the lateral and medial maleolous, a layer of rigid plaster, one to two layers of cast padding, a layer of fiberglass, a posterior splint that is fabricated out of a roll of fiberglass tape, unfurled and folded to be three to four layers thick when applied, a rigid walker plate, a rubber walker heel, and a final roll of fiberglass that the clinician will continue rubbing until the cast sets up, approximately ten to twelve minutes post application.

Even the casting system identified in U.S. Pat. No. 6,974,431 is the same as the original total contact cast configuration except in a kit form. There are inherent flaws that all of these accepted existing total contact casting systems have in common that have not been addressed.

Currently less than 2% of clinicians utilize total contact casting to treat their diabetic and neuropathic foot ulcer patients. Past objections to total contact casting were the time it takes to apply, the cost of materials, consistency of application, weight of a cast, and patients developing back and hip pains due to the change in the length of the leg which greatly effects the body mechanics of these already compromised patients.

In addition to the diabetic and neuropathic ulceration application, this versatile system can be utilized as a serial casting system for improving the range of motion for burn, cerebral palsy, spinal bifida, spinal cord injury, muscular dystrophy, idiopathic toe walking, and peripheral neuropathy patients. Applied weekly, gradually increasing the range of motion to a specific limb. This is a non-surgical approach aimed at reducing muscle tightness around the joint that is limiting the range of motion and functional mobility.

Other solutions in existence have merely tried to address the time of application and consistency issues without getting to the core of the problem. Jensen and Gillin developed a cast kit that incorporated all of the components that the clinician would typically assemble separately into one box. The components in the Jensen and Gillin system are essentially the same as any clinician would pull from their inventory with the exception of a unique felt pad that takes what would be two individual pads, the tibial crest and the maleoli pad and connected them as a one piece system. (U.S. Pat. No. 6,974,431)

There is an existing system that resembles a fiberglass sock. This system is not rigid, does not provide intimate contact to the leg, and has to be placed in a removable walker boot to support the system.

Other casting systems discovered during the patent search were designed for stabilizing fractured bones and not for the treatment of a specific condition such as diabetic and neuropathic foot ulcerations.

Currently serial casting consists of specific products that are assembled by a technician to accommodate the defect. This system is geared towards providing all of the components to accommodate a wide range of indications. Additionally this system is universal and will accommodate children to adults.

Conventional total contact casting systems tend to be time consuming, extend the length of limb, can create additional ulcerations, and are difficult to remove.

The Jensen and Gillin system follows the traditional total contact cast configuration with exception to the felt pad that they utilize over the tibia of the leg. Historically there was a separate pad that runs distally from just under the fibular head down to the dorsal aspect of the foot. Additionally there were two felt pads that covered the maleolous to protect them during removal. The pads are taped onto the stockinette while preparing for the cast. Jensen and Gillin connected the maleoli pads creating a one piece system. The Jensen/Gillin system is very time consuming and in most cases requires two clinicians to apply. Once the final roll of cast tape is utilized a clinician has to continue rubbing the fiberglass so that it doesn't un-roll while setting up. This requires approximately 20 minutes to apply and cure.

Another key factor that has effected the popularity of casting are complaints by the patients of hip and back pain. These systems are being utilized for five to eight weeks so the patient is in the cast for quite some time. Existing total contact casting systems utilize several rolls of padding, plaster, and fiberglass to build up the body of the cast. Prior to the application of the rubber walker heel and the last roll of fiberglass a thick rigid plate is placed on the plantar surface of the foot extending from the heel to just under the toes. This plate adds a significant amount of length to the cast as it is not just the thickness of the plate but the fact that it is being balanced at the heel and solace of the foot which are the high points of the plantar foot surface. The plate is utilized to help re-distribute the weight of the patient evenly over the entire foot. Subsequently the plate increases the length of the leg making it disproportionately longer than the other leg thus throwing off the natural body mechanics and causing hip and back pain. Prior systems tend to use traditional components that are very heavy which just exacerbate these conditions for the patient. The Jensen/Gillin system incorporates the heavy materials and a very thick walker plate which doesn't address the issues that have been associated with total contact casting for decades.

Total Contact Casting is meant to have very close contact with the patients limb. This is important in order to assure maximum pressure offloading to the ulcer and minimize movement in the cast. Prior systems utilize cast padding as the first layer covering the stockinette and felt tibial crest pad. This padding breaks down and compresses creating space within the cast. Subsequently, the foot pistons forward and backwards in the cast creating additional ulcerations and pressure points.

Contact Cast removal has been a long standing issue and in several cases where patients have ended up with serious injuries as a result. Prior total contact casting systems are cut down the center of the tibia, over the tibial crest pad, along the dorsum of the foot, over the toes, and then wedges are cut over the maleoli pads. The cast has to spread at the center while supporting the leg with opposing pressure until the cast breaks. This requires a lot of strength and can be very time consuming. Occasionally patients have excessive swelling and end up at the emergency room for removal. A traditional below the knee cast cuts on the lateral and medial sides of the leg with the center removing so the cast literally falls off of the leg. There have been numerous situations where patients have gone to emergency and since the typical doctor is not familiar with the total contact cast removal have cut into and burned the patients legs. None of the prior systems have addressed this chronic struggle up to this time.

There are no known existing serial casting systems commercially available for clinicians to utilize.

It is therefore an object of the invention to provide a turn key, user friendly casting system.

It is another object of the invention to provide a versatile casting system that promotes consistency of application.

It is another object of the invention to provide a casting system that can be utilized for a variety of defects and conditions.

It is another object of the invention to provide a casting system that produces re-producible clinical outcomes.

SUMMARY OF THE INVENTION

In accordance with the present invention, there is provided a system that is clinically and effically sound, consisting of proprietary components that not only address the needs of the clinician but are universally utilized in a concise protocol covering a wide range of indications and conditions.

BRIEF DESCRIPTION OF THE DRAWINGS

A complete understanding of the present invention may be obtained by reference to the accompanying drawings, when considered in conjunction with the subsequent, detailed description, in which.

For purposes of clarity and brevity, like elements and components will bear the same designations and numbering throughout the Figures.

DESCRIPTION OF THE PREFERRED EMBODIMENT

Figure 1:
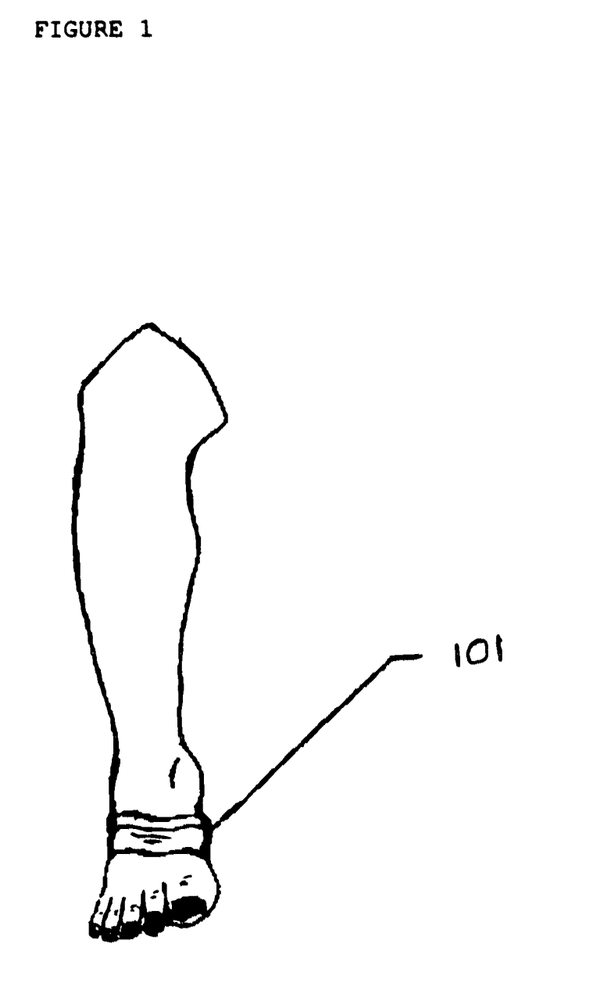
FIG. 1 is a front view of a patient's leg and foot with a wound dressing covering the defect.

FIG. 1 is a front view of a patient's leg dressed and ready for cast preparation.

Figure 2:
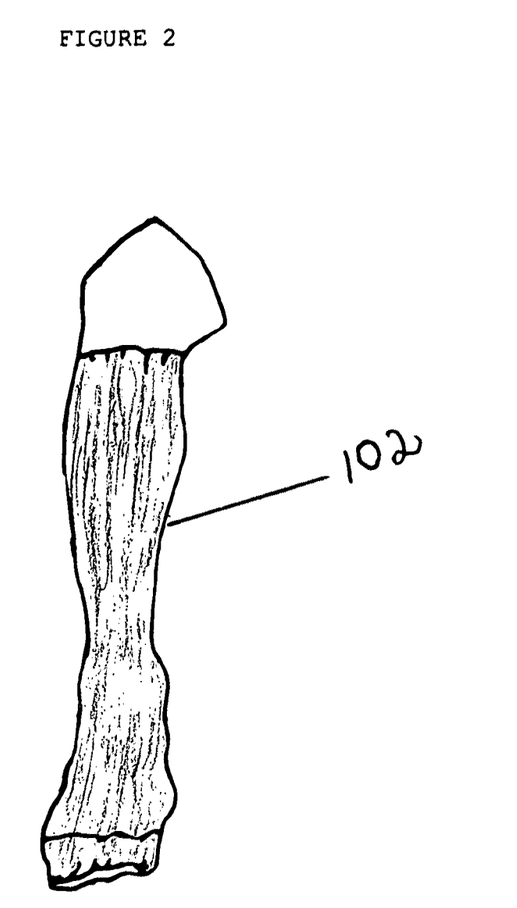
FIG. 2 is a front view of a patient's leg and foot with first layer which is a protective stocking.

FIG. 2 is a front view of a patient's leg with the first protective initial leg cover.

Figure 3:
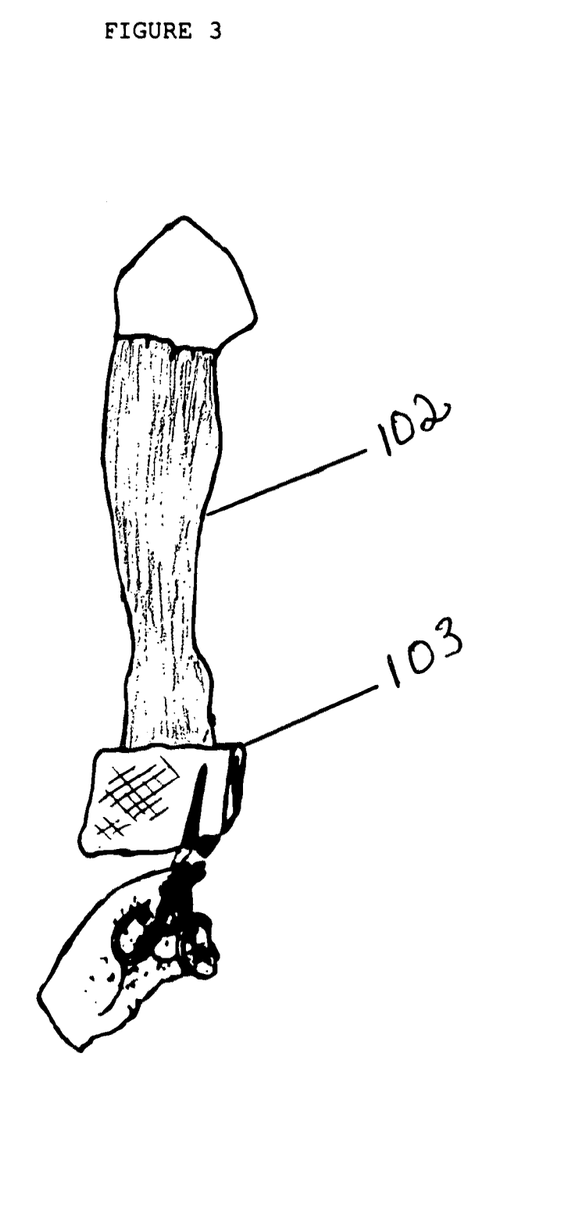
FIG. 3 is a front view of a patient's leg covered with a stocking and the self adhesive protective toe cover applied and trimmed to the contour of foot.

FIG. 3 is a front view of a patient's foot with proprietary toe protector, trimmed to fit contour of the foot.

Figure 4:
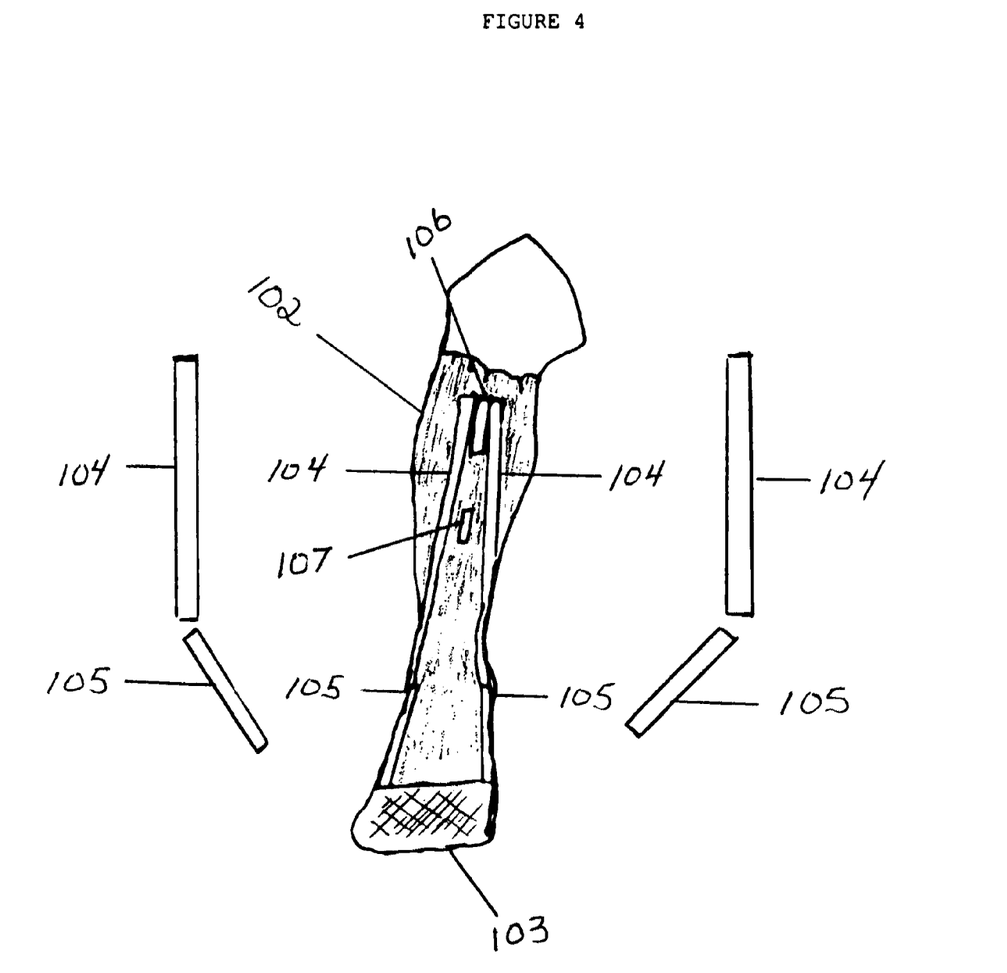
FIG. 4 is a front detail view of a patients leg and foot ready to cast, prepared with the stocking, toe protector, lateral and medial offloading strips, maleoli strips, tibial bridge, and mid-tibial pad.

FIG. 4 is a front detail view of a patient's leg prepared with proprietary felt lateral and medial offloading and maleoli strips.

Figure 5:
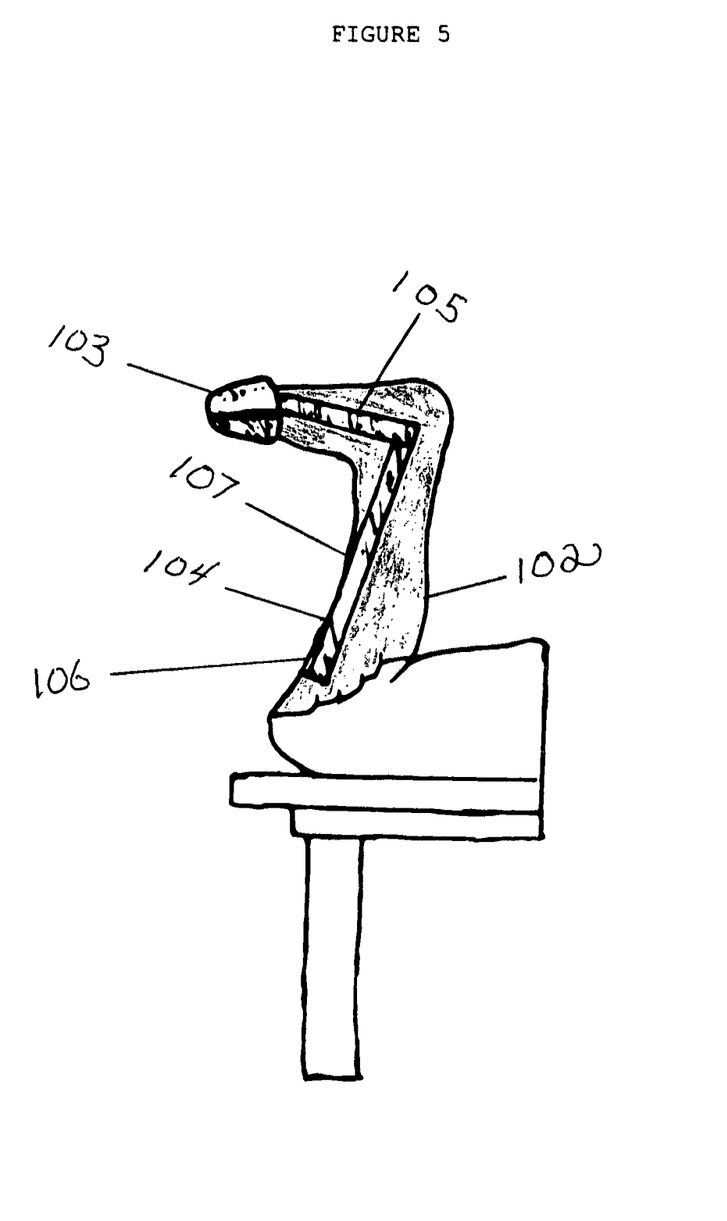
FIG. 5 is a right detail view of a patient's leg and foot in the prone position, prepared for casting.

FIG. 5 is a right detail view of a patient's leg in prone position, prepared for casting.

Figure 6:
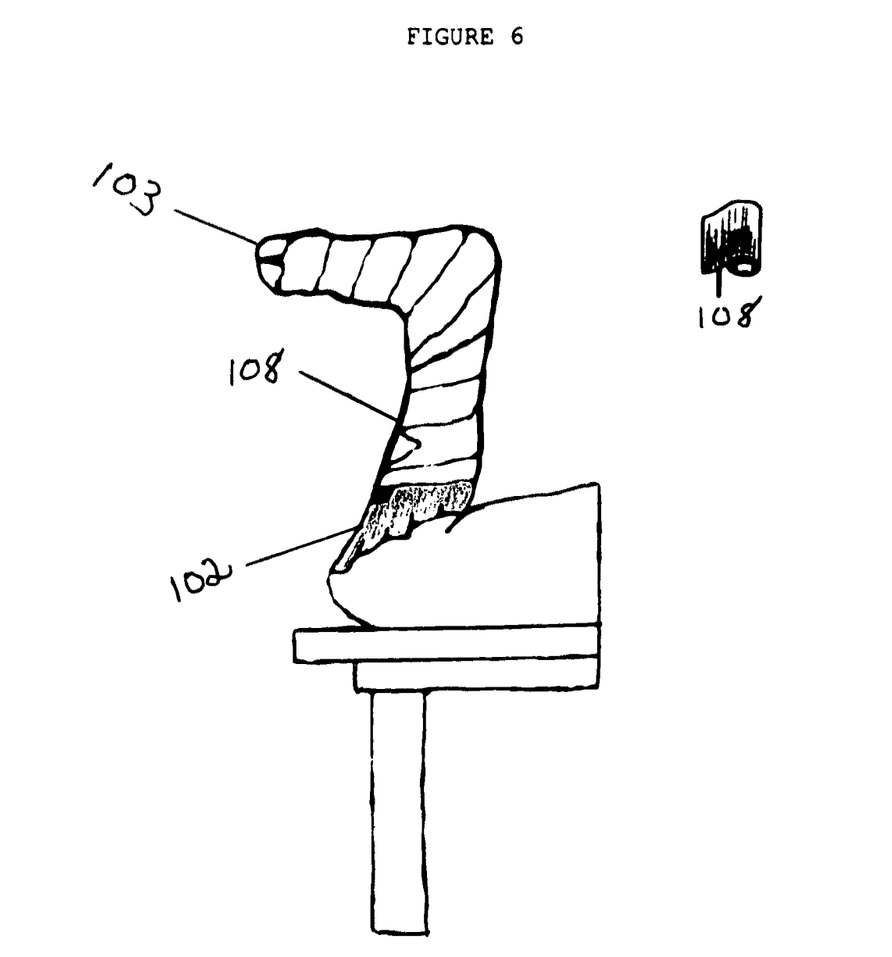
FIG. 6 is a right detail view of a patients leg and foot with the first roll of elastic plaster applied over the stocking, foam toe protector, and proprietary felt offloading and maleoli strips, providing intimate contact with the leg.

FIG. 6 is a right detail view of a patient's leg with initial roll of elastic plaster casting material.

Figure 7:
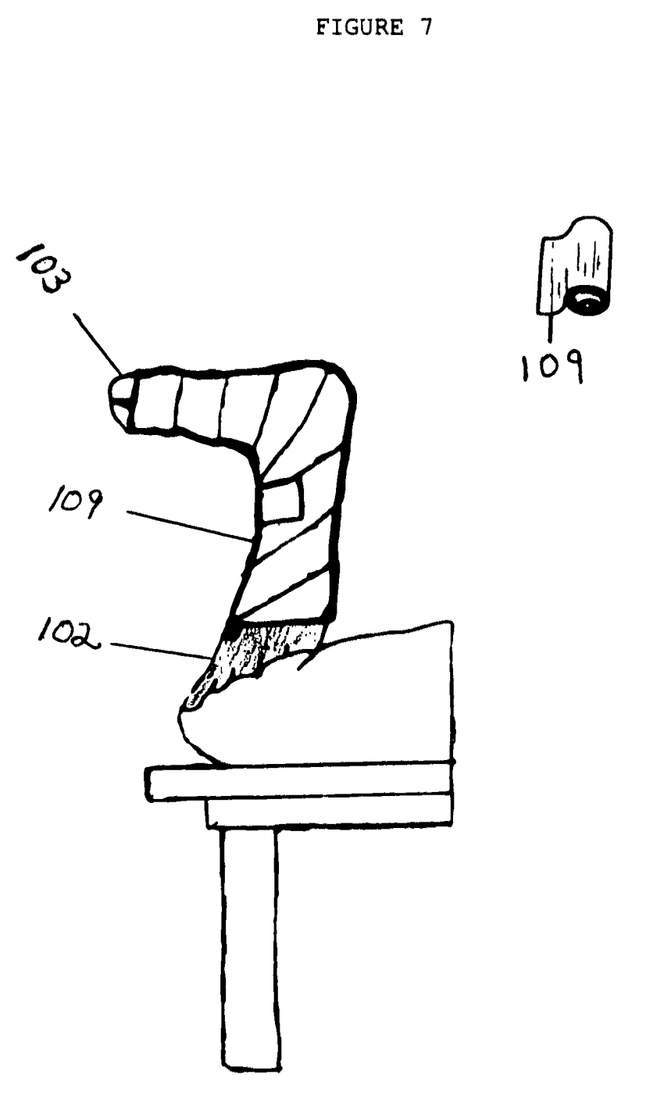
FIG. 7 is a right detail view of a patient's leg and foot with first roll of fiberglass tape covering the elastic plaster, essential for the correct positioning of the foot providing a rigid shell adding strength to the cast.

FIG. 7 is a right detail view of a patient's leg with first roll of fiberglass that is wet and rolled to cover to just below fibular head.

Figure 8:
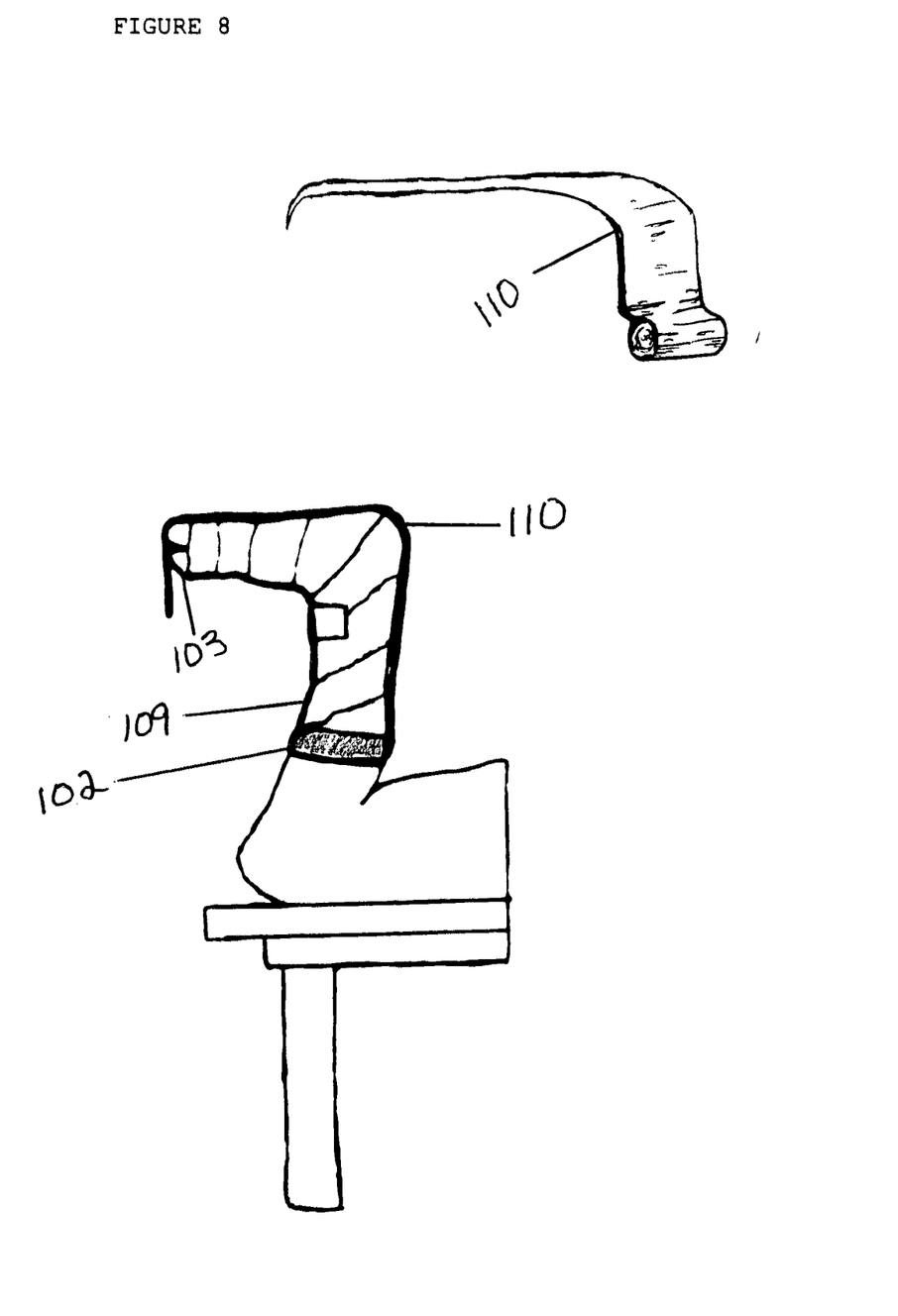
FIG. 8 is a right detail view of a patient's leg and foot with the extra strength pre-fabricated posterior splint covering the planter surface hanging over the posterior aspect of the leg and secured at the proximal end with the excess stocking.

FIG. 8 is a right detail view of a patient's leg with the proprietary extra strength pre-fabricated splint.

Figure 9:
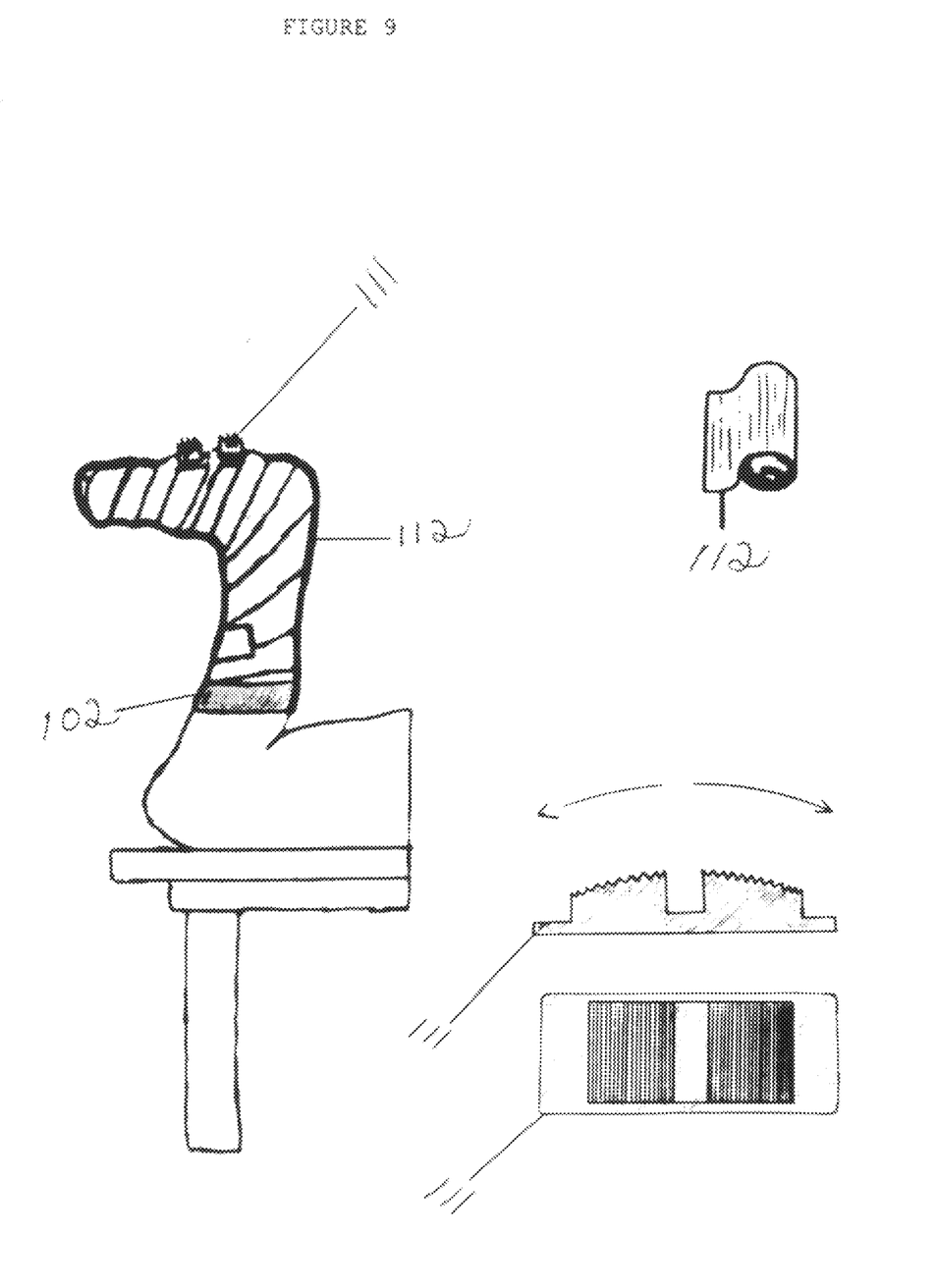
FIG. 9 is a right detail view of a patients leg and foot with the final roll of fiberglass tape applied, securing the proprietary rocker walker, aligned with the anterior tibia, while forming the pre-fabricated posterior splint to the patients limb providing maximum support to the foot and ankle.

FIG. 9 is a right detail view of a patient's leg and foot with final roll of fiberglass securing proprietary rubber rocker walker.

Figure 10:
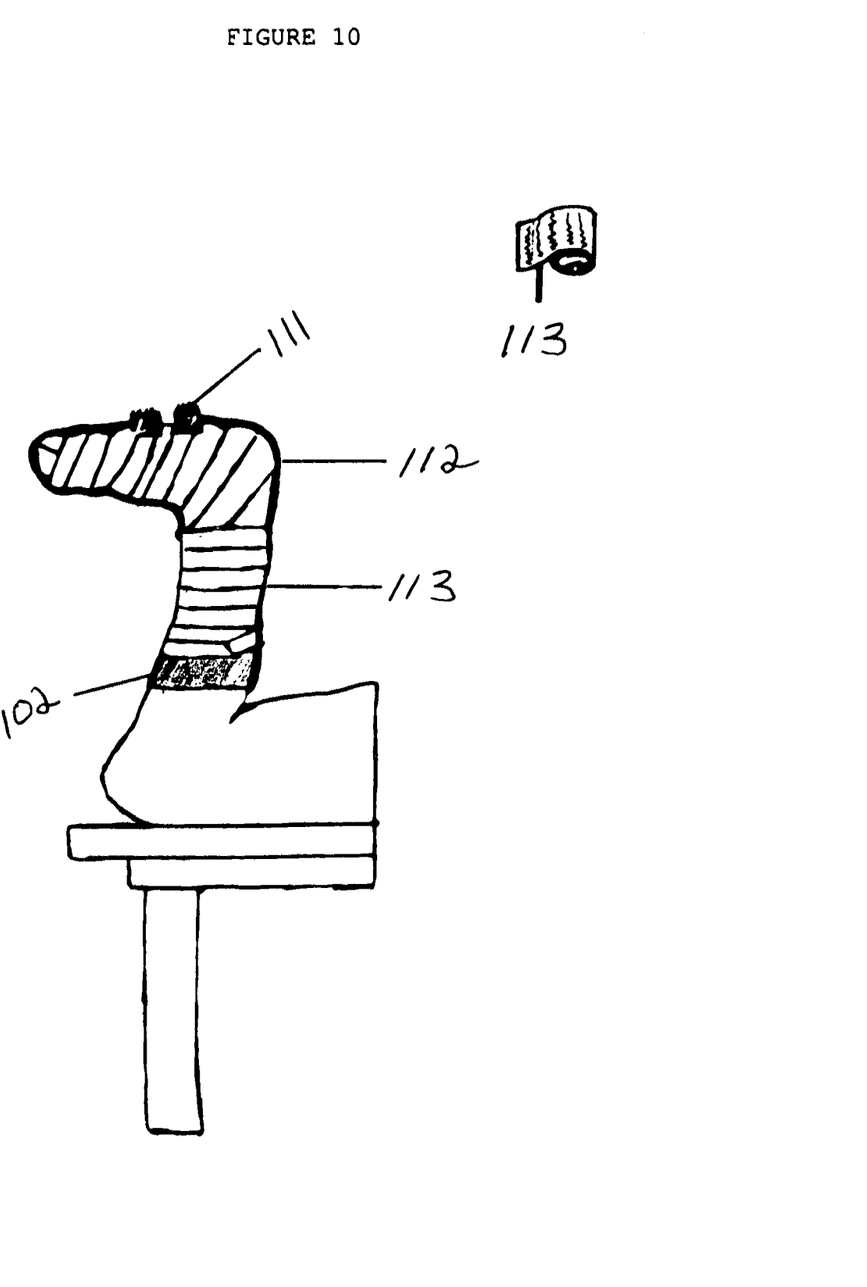
FIG. 10 is a right detail view of a patient's leg and foot with a completed cast application, and the self adhering dressing securing the loose end of the fiberglass tape.

FIG. 10 is a right detail view of a patient's leg with finished cast.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

DETAILED DESCRIPTION OF THE INVENTION

Referring to the figures, in which like reference numbers refer to like components thereof, FIG. 1 shows the foot of the patient covered by wound dressing 101. FIG. 1 is an example of a wound dressing application. A high percentage of diabetic and neuropathic patients will develop foot ulcerations. These patients have little or no feeling resulting in insufficient sensory feedback so they are unable to adjust the gait for the insensate foot causing tissue damage and ulcerations on the plantar surface. If these types of defects are left untreated they often require subsequent amputation of the limb.

There is science based evidence that supports the methodology of offloading pressure from the wound removing the propulsive forces that stall the healing process. In the late 1930's a method of applying a rigid cast with little padding was introduced and was recognized as the "Gold Standard" for treating plantar surface ulcerations. There have been many concerns and issues relating to this modality that have led to underutilization amongst clinicians. The apparatus and method of the present invention addresses all of these concerns making the application more comprehensive, leading to faster wound healing times. In addition, the present invention accommodates deformities such as valgus, varus, equinus, and charcot foot which make up a large percentage of patients with plantar ulcerations.

FIG. 2, illustrates a patients leg with the first layer 102, is the first protective layer, consisting of a cotton tube stocking that covers the leg circumferentially allowing subsequent components to be attached. The cotton tube stocking covers above the knee distally and folded over the toes.

FIG. 3, illustrates the patients leg with protective self-adhesive perforated foam toe pad. 103, the self adhesive perforated foam toe pad 103, is applied over the distal toe area to protect the toes from potential cast abrasions. The self-adhesive foam toe pad 103, is perforated to allow air to moisture transfer keeping the toes dry reducing risk of maceration and fungal infection. The self-adhesive perforated foam toe pad 103, is placed over the distal toes covering distal end of cotton tube stocking 102, evenly distributing the perforated self adhesive foam toe pad 103, over the dorsum to the plantar surfaces and is trimmed to fit the contour of the lateral and medial sides of the foot.

FIG. 4, illustrates the patients leg with the self-adhesive felt lateral and medial strips 104, secured from the proximal tibia just below the tibial tuberosity to the bottom of the malleolus attached to the cotton tube stocking 102, with the self-adhesive felt maleoli strips 105, overlapping the distal end of the self-adhesive felt lateral and medial strips 104, connecting to the proximal edge of the self-adhesive perforated foam toe pad 103. The proximal tibia is lined with a self-adhesive felt tibial crest bridge 106, and distally with additional self adhesive felt strips 107, to protect the tibial crest to the talus area of the foot. The unique configuration of felt strips protects all of the bony prominences that typically become pressure points, causing tissue degradation and additional ulcerations. Traditionally a single wide protective strip is applied over the tibial crest and patches are applied over the malleolus. By utilizing self-adhesive felt lateral and medial strips 104, and overlapping the self-adhesive felt maleoli strips 105, more of the patient's surface area is protected reducing the risk of additional ulcerations, also making the cast removal much easier and faster.

FIG. 5, illustrates the patients leg in the prone position consisting of the cotton tube stocking 102, self-adhesive perforated foam toe pad 103, self-adhesive felt lateral and medial strips 104, self-adhesive felt maleoli strips 105, self-adhesive felt tibial bridge 106, and self-adhesive felt tibial crest strips 107. The patient is placed in the prone position as it reduces the incidence of toe-drop which can lead to improper cast application. It is important that the foot is secured in a ninety degree position for proper application and offloading. The present invention is unique as it removes in a bi-valve configuration meaning that the cast can be removed with a cast cutting saw by making parallel cuts on the lateral and medial sides of the leg and down the center of the self-adhesive felt lateral and medial strips 104, which can be easily identified by the ridges on either side of the cast. Cuts are then made distally across the self-adhesive lateral and medial maleoli strips 105, and over the distal toe area. The center of the cast is pulled free allowing for the cast to easily be removed from the patient's leg.

FIG. 6, illustrates the patients leg in the prone position prepared for the first rigid layer after the felt and cast padding which is fine plaster or fiberglass 108, casting material commonly referred to as the egg shell layer. The first plaster layer 108, is the basis for intimate contact and is the layer that contours to the protective components. The first layer 108, eliminates the risk of the protective felt strips floating and creating a pathway for shear forces that can lead to secondary ulcerations.

FIG. 7, illustrates the patients leg in prone position, with the said first layer of a fiberglass 109, applied over the said plaster 108, and is applied by hydrating the material, rolling circumferentially from the distal edge of the plaster first layer 108, up the leg to the proximal edge of the first plaster 108. The said first fiberglass layer 109, of casting material is applied providing strength to the cast. The cotton tube stocking 102 at the proximal end of the cast is left exposed so it can later be folded down to create a soft collar.

FIG. 8, illustrates the patients leg in prone position and the multi-layer prefabricated support splint 110, being applied over the said first fiberglass layer 109. The multi-layer prefabricated support splint 110, is applied between the said first fiberglass layer 109, and the said second fiberglass layer 112. The multi-layer prefabricated support splint 110, is applied starting at the proximal edge of the posterior side of the cast, down the leg, across the plantar surface, overhanging at the toes and around the self-adhesive perforated foam toe pad 103. The excess cotton tube stocking 102, is rolled over the top of the multi-layer prefabricated support splint 110, to secure it in place and create a soft collar around the proximal rim of the cast. The excess multi-layer prefabricated support splint 110, material overhanging at the toes can be trimmed off in strips to level the rocker/walker 111, accommodating patients with specific anatomic foot defects. Traditionally a clinician will fabricate a splint by taking a fiberglass roll, unrolling it and folding it into approximately 3 layers. The present invention contains a multi-layer prefabricated support splint 110, that is prefabricated and the equivalent thickness of two and a half traditional support splints adding significant structural integrity. The added strength of the support splint reduces the number of layers needed to cast a patient as well as application times.

FIG. 9, illustrates the patients leg in the prone position with rocker/walker 111, in position for attachment after said second fiberglass layer 112. The rocker/walker 111, is Positioned with the front of the back walker pad in alignment with the anterior tibia of the leg and sitting directly on the prefabricated multi-layer support splint 110. There is front to back orientation to the rocker/walker 111, designed to promote normal bio-mechanics during ambulation. Typically a cast utilizes a plate that lies on the plantar surface to accept the walker heel. The current invention has eliminated the walker plate by designing an extremely thick multi-layer prefabricated support splint 110, that will accept the rocker/walker 111. The said second layer of fiberglass 112, is utilized to secure the rocker/walker 111, while adding additional strength the cast. The said second layer of fiberglass 112, is applied by hydrating the material, starting at the styloid process distally around the toes, circling the heel and back around until fiberglass overlaps. When adjacent to the metatarsal head the fiberglass is rolled circumferentially over the dorsum, securing the loose end of the multi-layer prefabricated support splint 110, than pinning the front of the rocker/walker 111 circumferentially around the foot and twisting the fiberglass to create a rope effect, running through the rocker/walker 111, center, around the heel securing the back of the rocker/walker 111, and proximally up the leg to the edge of the cotton tube stocking 102. The elimination of the traditional walker plate lowers the length of limb or cast length significantly and promotes normal ambulation.

FIG. 10, illustrates the patients leg in the prone position with the completed cast ready to receive the said self adhering dressing 113, to finish the cast. The self adhering dressing 113, is utilized to secure the loose end of said second fiberglass layer 112, starting at the edge of the said cotton tube stocking 102, rolling distally towards the said rocker/walker 111, until roll is utilized.

Having thus described the invention, what is desired to be protected by Letters Patent is presented in the subsequently appended claims.

What is claimed is:

1. A method for applying a new cast on patients with diabetic and neuropathic foot ulcerations comprising applying a bandage to protect the wound area, applying a cotton tube stocking over the leg, foot and a folded area over the toes, positioning a perforated self-adhesive foam toe pad over the distal toe area evenly distributed over the dorsum and plantar foot surfaces, positioning a self-adhesive felt strip on a lateral and a medial side of the leg at the bottom of the malleolus, parallel and proximally up the leg to just below the tibia tuberosity, positioning a self-adhesive felt tibia bridge connecting the proximal inside edges of the self-adhesive felt lateral and medial strips, positioning a short self-adhesive felt malleoli strip on the lateral and medial side of the foot from the edge of the self-adhesive foam toe pad, proximally up the foot overlapping the distal end of the lateral and the medial strip to the back of the malleolus, positioning the self-adhesive felt strips covering the tibia crest from distal edge of self-adhesive tibia bridge to the talus, applying a plaster shell from the middle self-adhesive foam toe pad, proximally to the edge of self-adhesive felt lateral and medial strips, applying a fiberglass layer over the plaster shell, applying a multi-layer prefabricated fiberglass support splint over the initial fiberglass layer from the upper posterior edge of the cast distally down the leg and over the entire plantar surface, securing a rocker, walker cast heel to the fiberglass support splint on the plantar surface with a final layer of fiberglass, applying a layer of self-adhering bandage over the upper one third of the cast, wherein the improvement comprises:

(a) applying a cotton tube stocking rolling from the distal toes, proximally up the leg to above the patient's knee leaving approximately four inches overlapping the toes, (b) applying the first self-adhesive felt lateral strip positioned at the base of the lateral malleolus proximally up the leg to just below the tibia tuberosity over the said cotton tube stocking on the leg;

(c) applying the second self-adhesive felt medial strip positioned at the base of the medial malleolus proximally up the leg to just below the tibia tuberosity and parallel to the first lateral self-adhesive felt strip over the said cotton tube stocking on the leg;

(d) applying the self-adhesive felt tibia bridge connecting the proximal inside edges of the first and second self-adhesive felt lateral and medial strips over the said cotton tube stocking on the leg;

(e) applying the first self-adhesive felt lateral malleoli strip connected at the proximal lateral edge of the self-adhesive perforated foam toe pad along the lateral side of the foot and overlapping the distal edge of the said first self-adhesive felt lateral strip, covering the malleolus over the said cotton tube stocking on the foot;

(f) applying the second self-adhesive felt medial malleoli strip connected at the proximal medial edge of the self-adhesive perforated foam toe pad along the medial edge of the foot and overlapping the distal edge of the second said self-adhesive felt medial strip and covering the malleolus over the said cotton tube stocking on the foot.

2. A method according to claim 1, wherein the first and second self-adhesive felt lateral and medial strips join at the proximal inside edge with the self-adhesive felt tibia crest bridge which connects with the self-adhesive felt tibia strips, and the self-adhesive felt lateral and medial malleoli strips join at the edge of the perforated self-adhesive toe pad and overlap at the distal end of the first and second self-adhesive lateral and medial felt strips positioning the self-adhesive felt strips in a parallel position on both sides of the foot and leg with a protective strip down the center of the tibia from the distal edge of the self-adhesive tibia bridge to the talus.

3. A method according to claim 1 for applying the cast comprising applying a plaster shell over the leg and foot covering the first and second self-adhesive felt lateral and medial strips, the self-adhesive felt tibia crest bridge, said self-adhesive felt tibia strips, said first and second self-adhesive felt lateral and medial malleoli strips from the middle of the self-adhesive perforated foam toe pad to the proximal edge of the self-adhesive felt lateral and medial strips, said self-adhesive felt tibia crest bridge any excess of said cotton tube stocking above proximal edge of the cast;

(a) applying the first fiberglass layer over the plaster shell starting at the distal edge of the plaster, rolling up the leg to the proximal edge of the plaster shell;

(b) applying the fiberglass pre-fabricated multi-layer support splint from the proximal edge of the posterior side of the leg, distally over the heel and along the entire plantar surface, overhanging at the distal toes;

(c) applying the second fiberglass layer starting at the medial mid foot rolling distally around the self-adhesive perforated foam toe pad around the lateral foot circling the heel, over the fiberglass pre-fabricated multi-layer support splint, back along the medial foot, overlapping and then rolling over the dorsum of the foot at the metatarsal heads, continuing proximally, twisting the fiberglass to create a rope effect securing the rocker, walker to the fiberglass pre-fabricated multi-layer support splint on the plantar surface up the leg, finishing at the proximal edge of the cast;

(d) applying the self-adhering bandage over the proximal edge of the cast and rolling distally one third of the way down the leg.

4. A method for applying a cast, the method comprising applying a cotton tube stocking over the leg, foot and a folded portion over the toes, positioning a perforated self-adhesive foam toe pad over the distal toe area evenly distributed over the dorsal and plantar foot surfaces, positioning the first self-adhesive felt lateral strip from the base of the lateral malleolus proximally up the leg to just below the tibia tuberosity, applying the second self-adhesive felt medial strip positioned at the base of the medial malleolus proximally up the leg to just below the tibia tuberosity, applying the self-adhesive felt tibia bridge connecting the proximal inside edges of the first and second self-adhesive felt lateral and medial strips, applying additional self-adhesive felt strips distally from distal edge of the self-adhesive felt tibia bridge covering the tibia crest and the talus area of the foot, applying the first self-adhesive felt lateral malleoli strip connected at the proximal lateral edge of the self-adhesive perforated foam toe pad along the lateral side of the foot and overlapping the distal edge of the first lateral strip and covering the malleolus, applying the second self-adhesive felt medial malleoli strip connected at the proximal medial edge of the self-adhesive perforated foam toe pad along the medial edge of the foot and overlapping the distal edge of the second self-adhesive felt medial strip and covering the malleolus, applying a plaster shell rolling from middle of the self-adhesive foam toe pad, proximally to the edge of self-adhesive felt lateral and medial strips and self-adhesive tibia bridge, applying a first layer of fiberglass starting at middle of self-adhesive perforated foam toe pad rolling to the proximal edge of a cotton tube stocking, applying pre-fabricated multi-layer support splint covering the posterior side of leg and along the plantar surface, applying a second fiberglass layer covering foot and leg securing the multi-layer support splint and rocker, walker in proper position, application of the self-adhering bandage to the proximal one third of the cast, comprising the steps of:

(a) applying the fiberglass pre-fabricated multi-layer support splint to the posterior side of the leg and the plantar surface increasing surface area, strengthening the cast; and (b) applying the said pre-fabricated multi-layer support splint to the proximal posterior edge of the cast, distally along the posterior side of the leg, over the heel, along the plantar surface and overhanging at the toes, and ready for receiving said rocker, walker heel, wherein attached directly to the said pre-fabricated multi-layer support splint.

5. A method according to claim 4, wherein said securing comprises of the following steps of;

(a) securing the proximal end of the fiberglass pre-fabricated multi-layer support splint by rolling an excess end of said cotton tube stocking over the splint securing the proximal end of said pre-fabricated multi-layer support splint and creating a soft collar;

(b) placing said rocker, walker on the plantar surface directly on to the pre-fabricated multi-layer support splint, and apply said second layer of fiberglass from mid-foot around toes circling the foot and rolling proximally to cast edge securing the said pre-fabricated multi-layer splint to the foot and leg.

6. A method according to claim 4, applying rocker, walker comprises the following steps of;

(a) positioning the rocker, walker heel on the plantar surface, to said fiberglass pre-fabricated multilayer support splint with front of the back said rocker, walker heel in alignment with the anterior tibia making sure that the orientation is correct with said rocker, walker heel, (b) securing said rocker, walker heel to said fiberglass pre-fabricated multi-layer support splint with said second fiberglass layer rolling from mid-foot encircling the toes around the heel and under the dorsum of the foot at the metatarsal heads, proximally securing the front of said rocker, walker, twisting the fiberglass creating a rope effect, pulling through said rocker, walker heel centered around the foot securing back of said rocker, walker heel, and to the proximal edge of the cast.

7. A method according to claim 4, applying said self-adhering bandage comprises the following steps of;

(a) applying the self-adhering bandage to secure loose end of said second fiberglass layer by starting at the proximal edge of the cast circling the cast distally one third of the distance between the proximal edge of the cast and the natural bend of the talus area.

8. A modality and system for casting a patient's diabetic and neuropathic plantar foot ulcerations and treating defects that limit range of motion comprising a first protective layer of cotton tube stocking adapted to cover the leg of the patient, the cotton tube extending from the knee to the foot of the patient, an adhesive foam perforated toe pad configured to be located and placed over the distal area of the toes, lateral and medial felt strips attached to the cotton tube stocking, a pair of felt malleoli strips attached to the cotton tube stocking and overlapping the distal ends of the medial and lateral felt strips and a first layer of plaster material covering the felt strips, said first layer of plaster becoming rigid to cover and protect the felt strips and the leg of the patient.

* * * * *